United States Patent [19]

Imura

[11] 4,446,871

[45] May 8, 1984

[54] OPTICAL ANALYZER FOR MEASURING A CONSTRUCTION RATIO BETWEEN COMPONENTS IN THE LIVING TISSUE

[75] Inventor: Kenji Imura, Osaka, Japan

[73] Assignee: Minolta Kabushiki Kaisha, Osaka, Japan

[21] Appl. No.: 216,526

[22] Filed: Dec. 15, 1980

[30] Foreign Application Priority Data

Jan. 25, 1980 [JP] Japan .................................. 55-8070

[51] Int. Cl.$^3$ ............................................... A61B 5/00
[52] U.S. Cl. .................................... 128/633; 128/664; 128/666; 356/41
[58] Field of Search ............... 128/633, 634, 665, 666, 128/664; 356/39–42

[56] References Cited

U.S. PATENT DOCUMENTS

3,922,088  11/1975  Lubbers et al. ....................... 356/40
4,305,398  12/1981  Sawa ...................................... 128/633

OTHER PUBLICATIONS

Merrick et al., Hewlett-Packard Journ., vol. 28, No. 2, pp. 2-9, Oct. 1976.

*Primary Examiner*—Kyle L. Howell
*Assistant Examiner*—John E. Hanley
*Attorney, Agent, or Firm*—Jackson, Jones & Price

[57] ABSTRACT

An optical analyzer such as oximeter is provided including a source of light having a plurality of different wavelengths. At least two or more of the different wavelengths have a fixed relationship of light absorption after coaction with hemoglobin oxide. The light is directed at the subject tissue and received after coaction by an optical probe. A first signal representative of the degree of light absorption at a predetermined standard wavelength is determined and then an attempt is made to match a second wavelength having a fixed relationship of light absorption to the predetermined standard wavelength, e.g., equal absorption, to generate a second signal representative of the second wavelength, whereby the amount of hemoglobin oxide can be determined in the bloodstream.

12 Claims, 8 Drawing Figures

OPTICAL ANALYZER FOR MEASURING A CONSTRUCTION RATIO BETWEEN COMPONENTS IN THE LIVING TISSUE

BACKGROUND OF THE INVENTION

1. Field of the Invention

The present invention generally relates to an electro-optical analyzer, such as an oximeter, for measuring a construction ratio between known components in living tissue, and more particularly to a non-invasive analyzer for optically analyzing living tissue without injuring it.

2. Description of the Prior Art

An optical oximeter for measuring the oxygen saturation of blood, which includes a construction ratio between the hemoglobin oxide ($HbO_2$) and the hemoglobin (Hb), has been known in the prior art. In such an optical oximeter, the oxygen saturation is determined by measuring the intensity of light transmitted through a living tissue by at least a pair of predetermined wavelengths and by subsequent processing of electrical signals representing the intensities of the pair of wavelengths of light.

The measured intensities of light, however are influenced not only by the absorption of the hemoglobin oxide and hemoglobin, but also by various noise factors. Therefore, it is generally necessary to remove such noise factors to provide a meaningful measurement.

Further, if a measurement is taken with reflected light, the light reflected from the living tissue would also include an additional or multiplying white noise factor due to surface reflection and/or light scattering in the non-blood tissue. Such white noise factors are quite difficult to be satisfactorily avoided or removed. In addition, the measured intensity would also be influenced by the relative movement of the probe to the living tissue.

Generally, in the prior art, the only optical oximeters that have been practical use light transmitted through a limited portion of tissue, e.g., an earlobe or a finger tip attached to an optical probe positioned on the opposite side from a light source.

An example of a prior art oximeter can be found in the Transactions on Biomedical Engineering, Vol. BME-22, No. 3, p. 183, May 1975: "The choroidal eye oximeter: an instrument for measuring oxygen saturation of choroidal blood in vivo.:

Additional prior art references can be found in U.S. Pat. No. 4,086,915, U.S. Pat. No. 3,825,324, U.S. Pat. No. 3,847,483, U.S. Pat. No. 3,787,124, U.S. Pat. No. 3,998,550, and U.S. Pat. No. 4,157,708.

The prior art is still seeking a simplified but accurate oximeter.

SUMMARY OF THE INVENTION

An object of the present invention is to provide an optical analyzer utilizing a novel concept of operation.

Another object of the present invention is to provide an optical analyzer capable of accurate measurement free from the influence of noise factors.

A further object of the present invention is to provide an optical analyzer of a reflection light measurement type.

A still further object of the present invention is to provide an optical analyzer widely applicable to various desired portions of living tissue.

An additional object of the present invention is to provide an optical analyzer wherein it is not necessary to directly contact the living tissue.

A still additional object of the present invention is to provide an optical analyzer capable of measurement even when the living tissue moves relative to the probe.

According to the present invention, the intensities of a source light, after contact with living tissue, are measured at various wavelengths. A wavelength $\lambda$ at which the intensity of light is equal to that of a predetermined standard wavelength $\lambda_0$ is searched, since the searched wavelength $\lambda$ depends on a construction ratio to be measured, such as hemoglobin oxide, the value of the construction ratio can be ascertained.

The present invention can take the form of an oximeter having a source of light with a plurality of different wavelengths, at least two or more of the wavelengths have a fixed relative relationship of light absorption after co-action with hemoglobin oxide, e.g., a predetermined standard wavelength and a second wavelength can have equal light absorption characteristics for a certain level of hemoglobin oxide. A fiber optical probe can direct the light at the subject tissue and return it for measurement after co-action and absorption by the tissue. A photodetector and supplemental circuitry are capable of generating a noise-free first signal representative of the degree of light absorption at the predetermined standard wavelength. Correspondingly, a plurality of electric signals representative of the degree of light absorption at the other scanning wavelengths are also generated. Appropriate circuitry or a microprocessor can select a second wavelength signal from the scanning wavelengths having a fixed relationship to the light absorption of the predetermined standard wavelength and generate a second signal representative of the second wavelength whereby the amount of hemoglobin oxide can be determined from a memory that stores the values of hemoglobin oxide with subsequent appropriate display.

The many attendant advantages of the present invention may be best understood by reference to the accompanying drawings in which like reference symbols designate like parts throughout the figures thereof.

DETAILED DESCRIPTION OF THE PREFERRED EMBODIMENT

The following description is provided to enable any person skilled in the field of electro-optical medical instrumentation to make and use the invention and sets forth the best mode contemplated by the inventor for carrying out his invention. Various modifications, however, will remain readily apparent to those skilled in the art, since the generic principles of the present invention have been defined herein specifically to provide a relatively simplified and easily manufactured electro-optical medical instrumentation to determine the level of hemoglobin oxide in living tissue.

The specific embodiment shown in the Figures is designed for use as an optical oximeter. The object living tissue schematically depicted is a human body containing known components of oxihemoglobin and deoxihemoglobin. A resulting construction ratio between these components can be obtained corresponding to the oxygen saturation of the human body.

Figure 1:
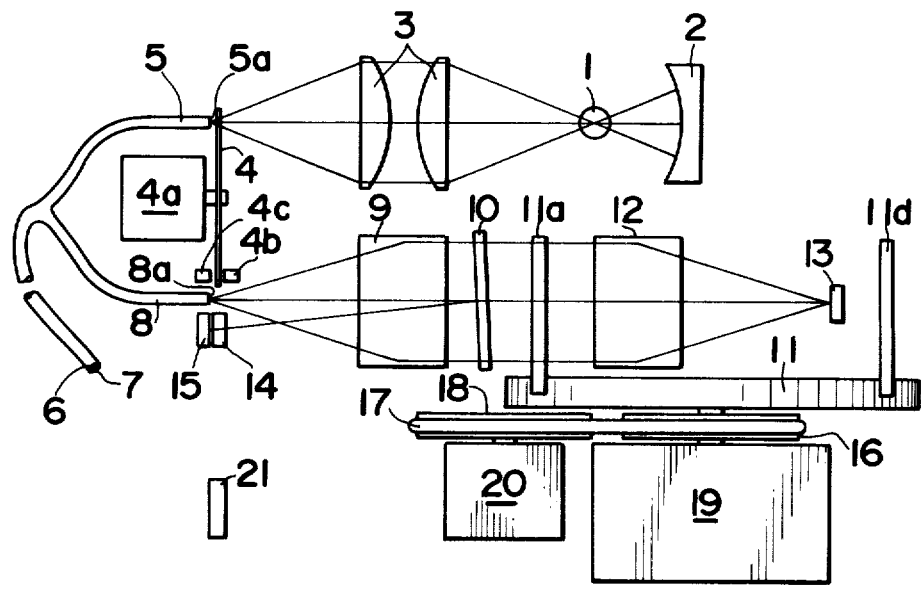
FIG. 1 represents a partially cross sectional schematic elevation view of the optical components of an embodiment of the present invention.
Figure 2:
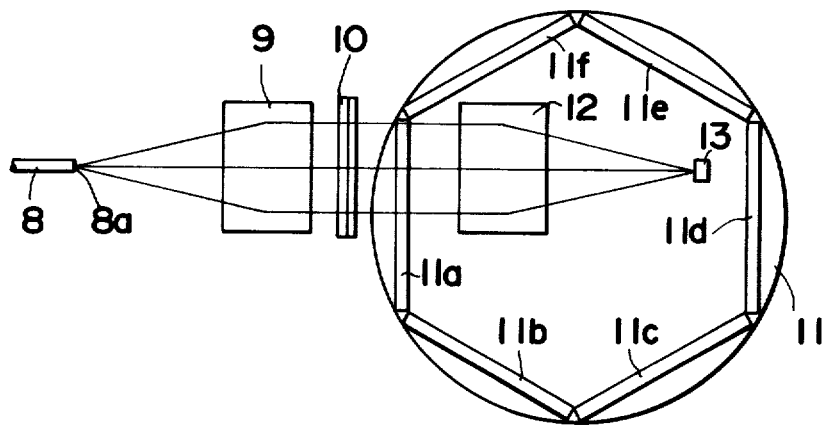
FIG. 2 represents a partially cross sectional schematic plane view of some optical components of FIG. 1.

FIGS. 1 and 2 represent a partially cross sectional schematic elevation view and a partially cross sectional schematic plane view of an optical system of an embodiment of the present invention, respectively. The light emitted from lamp 1 is convergently directed towards an entrance port 5a of an optical fiber guide 5 by means of a concave mirror 2 and a collimator 3 and is further segmented or chopped by a chopper 4 driven by a motor 4a. The timing of the chopping of the light entering into entrance port 5a due to chopper 4 is detected by the combination of a light emitting diode 4b and a phototransistor 4c. Other forms of monitors could also be utilized to provide timing signals. The optical fiber guide 5 leads to exit 6, forming a part of a medical probe, from which the light introduced from entrance port 5a emerges. A part of the light emerging from exit 6 returns back to a return entrance portion 7, which is surrounded by exit 6 after traveling through the living tissue, which is the subject of the analysis. Entrance 7 leads to an exit 8a by way of a second optical fiber 8. The light emerging from exit 8a is made parallel by collimator 9 and is partially reflected by dichroic mirror 10, which is slightly inclined with respect to the optical axis of collimator 9. The reflected light is directed convergent toward photocell 15 by means of collimator 9. Photocell 15 is located adjacent to exit 8a and is provided with band-pass filter 14 in front of it for the purpose of detecting the intensity of a standard wavelength of light.

The major portion of the parallel light passing through the collimator 9 towards dichroic mirror 10 is transmitted therethrough toward one of a number of band-pass filters (interference filters) 11a to 11f. These interference filters are mounted on the periphery of a rotary disc 11 for selectively positioning one of the band-pass filters on the optical axis of collimator 9 at various angles to the optical axis as seen in FIG. 2. After passing through one of band-pass filters 11a to 11f located on the optical axis, the light is made convergent toward photocell 13 by means of collimator 12. Rotary disc 11 can be driven by motor 20 through pulleys 16 and 18 and belt 17. The angle of rotation of rotary disc 11 is monitored or detected by a rotary encoder 19. Thus, one of band-pass filters 11a to 11f on the optical axis varies its angle with the optical axis in accordance with the rotation of rotary disc 11 for continuously changing the transmittable wavelength band with position being detected by rotary encoder 19. A plurality of band-pass filters are used to continuously change the wavelength to be detected by photocell 13 over a wide range because the variable range of only one band-pass filter is limited.

A white reflector 21 of a standard reflectance is measured prior to the measurement of an object for the purposes of calibrating the output of the device with respect to the various wavelengths scanned by band-pass filters 11a to 11f since the output of the device can be influenced by variable factors in the device, such as the spectral characteristics of the light source or the photocell.

By means of the above optical system, the light scattered through and reflected from the living tissue is detected at a standard wavelength by photocell 15 and at various other wavelengths by photocell 13 with the specific wavelength of light received by photocell 13 encoded by means of rotary encoder 19.

Figure 3:
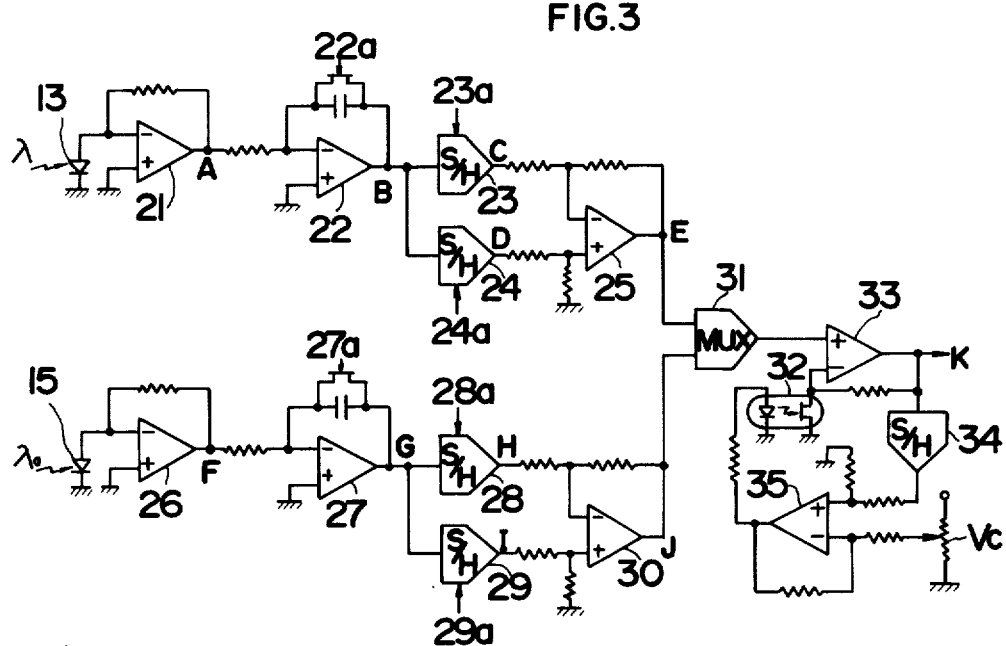
FIG. 3 represents a circuit diagram of an analog portion of the electric circuit of the invention.
Figure 4:
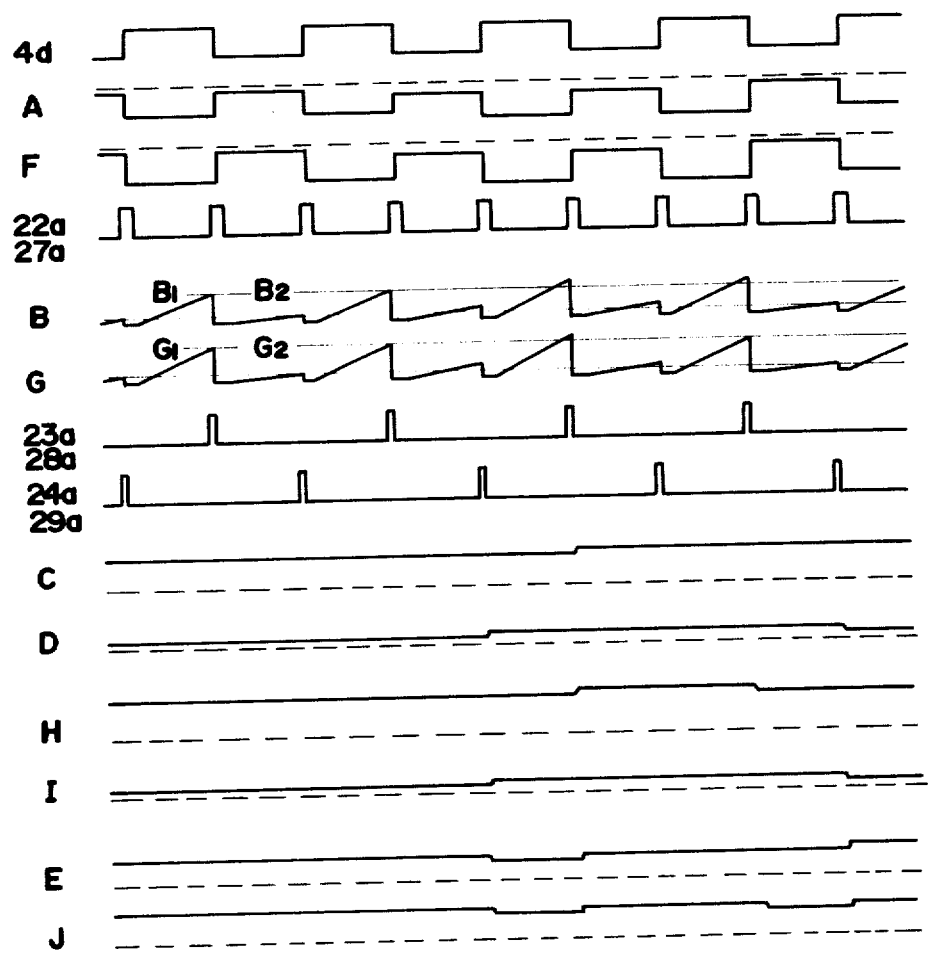
FIG. 4 represents a time chart showing the operation of the circuit of FIG. 3.

FIG. 3 represents a circuit diagram corresponding to an analog part of the electric circuit of the invention for processing the output signal of the above-described optical system, the operation thereof being shown in the time chart of FIG. 4. The output current of photocell 13, which receives the light of the variable scanning wavelength $\lambda$, is converted into a corresponding voltage signal A by means of current-voltage converter 21. The voltage signal A is integrated for a predetermined period of time to produce signal B by means of integrating circuit 22 which is periodically switched on and off by a signal 22a synchronized with a signal 4d from phototransistor 4c indicative of the timing of chopping by chopper 4. (The actions of the signals will be better understood by reference to FIG. 4.) In the signal B, a part $B_1$ integrated within a time period, in which chopper 4 allows a light passage, would include both a signal component and a noise component, while a part $B_2$ integrated within another time period, in which light is blocked by chopper 4, would include only the noise component. The part $B_1$ is successively stored by sample hold circuit 23 controlled by sampling signal 23a. On the other hand, the part $B_2$ is successively stored by sample hold circuit 24 under the control of sampling signal 24a. Thus, the output C of sample hold circuit 23 includes both signal and noise components, and the output D of sample hold circuit 24 a noise component only. Output D is subtracted from output C at a succeeding subtraction circuit 25 to form signal E in which the noise component is eliminated.

In a similar manner, the output current of photocell 15, which receives the light of standard wavelength $\lambda_0$, is processed through current voltage converter 26, integrating circuit 27, sample hold circuits 28 and 29 and subtraction circuit 30 to obtain signal J.

Signals E and J are alternatively transmitted by AGC amplifier 33 under the control of a multiplexer 31. The automatic gain control of the AGC amplifier is accomplished in the following manner. Namely, sample hold circuit 34 is provided to store a signal component, which corresponds only to an amplified signal J, of output K of the AGC amplifier 33 (the sampling wavelength voltage is not stored). Further provided is a differential amplifier 35 for amplifying the difference between the output voltage of the sample hold circuit 34 and a given constant voltage Vc. The output of differential amplifier 35 controls photo-FET 32 to change its resistance, the output of photo-FET 32 being connected to the input terminal of AGC amplifier. Thus, the closed feedback loop composed of the above elements, 34, 35 and 32, controls the gain of the AGC amplifier so that the component of output K corresponding to signal J is held at a nearly constant voltage Vc irrespective of the value of signal J to establish a predetermined voltage level for subsequent conversion of a digital format.

According to the above analog circuit in FIG. 3, therefore, the output K alternatingly shows the light intensities at the standard wavelength $\lambda_0$ (corresponding to the J signal) and at the scanning wavelength $\lambda$ (corresponding to the E signal) in response to a predetermined time sequence from multiplexer 31.

Figure 5:
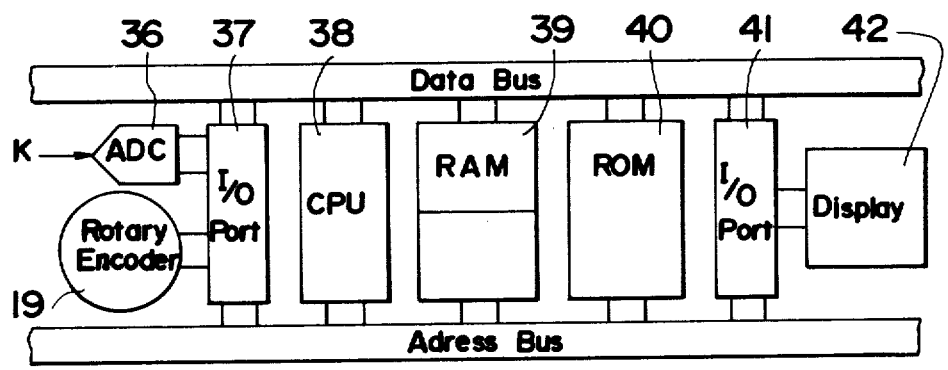
FIG. 5 represents a block diagram of a digital portion of the electric circuit of the invention.

FIG. 5 represents a block diagram of a microcomputer constituting a digital part of the electric circuit for processing the output signal of the optical system and connected to the above-described analog part. A-D converter 36 is for converting the components in analog signal K corresponding to standard wavelength $\lambda_0$ and scanning wavelength $\lambda$ into digital signals $D\lambda_0$ and $D\lambda$, respectively. A-D converter 36 as well as multiplexer 31 in FIG. 3 is controlled by CPU 38. The microcomputer in FIG. 5 processes as its input data the digital signals $D\lambda_0$ and $D\lambda$, and a digital output of the rotary encoder 19 indicative of the scanning wavelength $\lambda$. Read Only Memory (ROM) 40 previously stores the coordinates of the scanning wavelengths to be addressed by the output of rotary encoder 19 and the oxygen saturation values addressed by the number of a scanning wavelength. In FIG. 5, the microcomputer further includes a Random Access Memory (RAM) 39, Input and Output ports 37 and 41, and a display 42 for indicating the output of the microcomputer.

The following description will be directed to the function of the invention and the procedure of measurement.

(i) The probe formed by light exit 6 and entrance portion 7 is preparatorily applied to the standard white reflector 21.

(ii) CPU 38 readw the output of the rotary encoder 19 indicative of the rotation of disc 11 to successively address the numbers or coordinates of the scanning wavelengths. With respect to every number of the scanning wavelength, $(D\lambda)cal.k$ and $(D\lambda_0)cal.k$ are correspondingly read and stored in predetermined areas of RAM 39 in the order of the number of the scanning wavelength, wherein "cal." means "calibrating" and k represents the number of the scanning wavelength numbered from 1 to n. It is needless to say that $(D\lambda_0)cal.k$'s are all equal for various k's.

(iii) After the above preparatory measurement with respect to the standard white reflector, the probe is applied to an object to be measured, such as living tissue.

(iv) CPU 38 reads $(D\lambda)$ mes.k and $(D\lambda_0)$mes.k in the similar manner as in step (ii), wherein the "mes." means "measuring" and k represents the number of scanning wavelength. CPU 38 further obtains $D_k$ according to a process expressed by the following formula, which calibrates $(D\lambda)$mes.k and $(D\lambda_0)$mes.k with $(D\lambda)$cal.k and $(D\lambda_0)$cal.k and obtains a ratio between the values relating to wavelengths $\lambda$ and $\lambda_0$ as follows:

$$\frac{(D\lambda)mes \cdot k/(D\lambda)cal \cdot k}{(D\lambda_0)mes \cdot k/(D\lambda_0)cal \cdot k} = D_k$$

(v) CPU 38 stores every $D_k$ corresponding to each number of a scanning wavelength in predetermined storage areas of RAM 39, respectively.

(vi) CPU 38 further operates to search a number of the scanning wavelength at which $D_k=1$, and addresses ROM 40 by the searched number of the sanning wavelength to read out a corresponding oxygen saturation value.

(vii) Display 42 indicates the read out oxygen saturation value by means of digital display elements, and all $D_k$'s (k=1 to n) sotred in RAM 39 by means of a graphic display device.

As is easily recognizable from the above explanation, the above embodiment searches a wavelength $\lambda$ having an intensity equal to that of the standard wavelength $\lambda_0$ with respect to the light contacting the living tissue to determine an oxygen saturation value from the searched wavelength $\lambda$ by way of a previously calculated and stored relationship between the oxygen saturation value vs. a wavelength $\lambda$ having an intensity equal to that of the standard wavelength $\lambda_0$.

In the above embodiment, the interference filters 10 and 11a to 11f are used for the purpose of introducing into the optical system a sufficient light flux with a wide range of wavelength values. Further, the light of standard wavelength $\lambda_0$ is measured in synchronization with the measurement of every scanning wavelength $\lambda$ for the purpose of cancelling all possible noise factors, which could be caused in cause of a measurement wherein the probe does not directly contact the skin surface of the living tissue. In other words, the procedure of measuring the light of standard wavelength $\lambda_0$ with respect to every scanning wavelength $\lambda$ is not necessary from a theoretical view of obtaining the necessary information of light intensity of standard wavelength $\lambda_0$ since it is theoretically equal with respect to all scanning wavelengths.

Therefore, as an alternative structure to the above embodiment, the standard wavelength may be selected fron the scanning wavelengths. Namely, $(D\lambda)$mes k/$(D\lambda)$cal k=$D'_k$ may be stored in RAM (39) with respect to all k's (k=1 to n). And, if a wavelength, the number k of which is j. is selected, a $D'_k$ having a value equal to $D'_j$ is searched to address ROM 40 from the number k of the searched $D'_k$. Even in this case, however, the synchronized measurement of an identical wavelength of light with respect to every scanning wavelength is still recommended for cancelling any possible noise.

The above alternative structure discloses that a standard wavelength is not necessarily selected from wavelengths other than the scanning wavelengths, but can be from the scanning wavelengths. This means that two or more standard wavelengths can be selected (as described later) simply by modifying the software of the microcomputer without further complicating the optical system to obtain two or more standard wavelengths. In other words, a pair of standard wavelengths, the number k of which are respectively 1 and m, can be selected from the scanning wavelengths numbered k=1 to n without modifying the optical system.

Figure 6A:
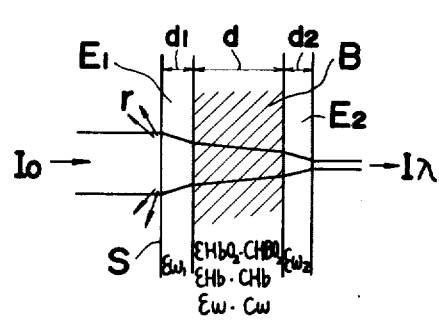
FIGS. 6a and 6b represent cross sectional views of a conceptional representation of living tissue for the cases of transmitted light measurement and reflected light measurement, respectively.
Figure 6B:
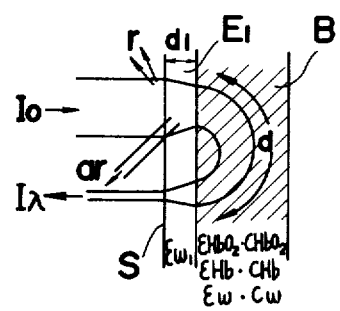
Figure 7:
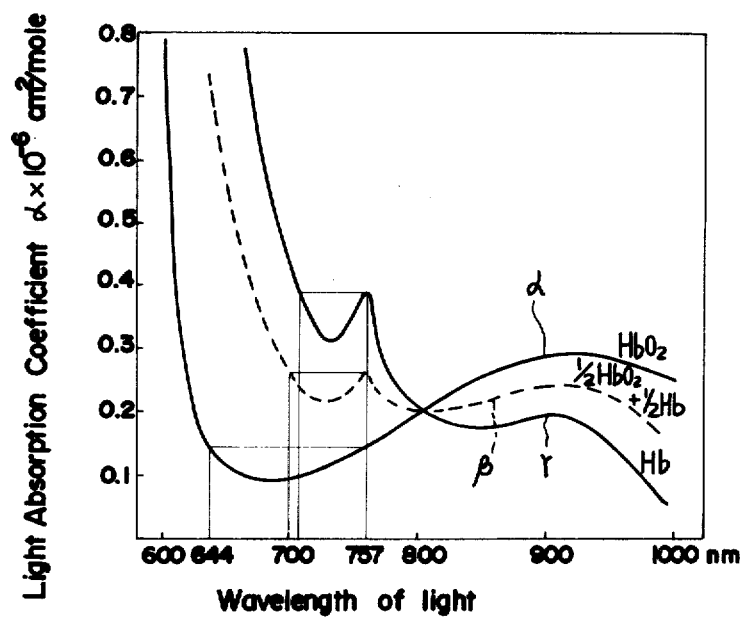
FIG. 7 represents a graph of wavelength versus the light absorption coefficient of the present invention.

The description of the invention will now be further advanced by an explanation of the theoretical analysis of why oxygen saturation can be obtained by the above measurements in connection with FIGS. 6 and 7.

The measured intensity I$\lambda$ of light of a scanning wavelength $\lambda$ which is incident on the living tissue and reflected by or transmitted through the same is expressed as follows:

(a) In case of transmission (See FIG. 6a):

$I\lambda = I_0(1-r)e^{-\epsilon\omega 1 \cdot d1} \cdot e$ $$-\epsilon\omega^{2\cdot d}\cdot e^{-(\epsilon HbO2\lambda.CHbO2+\epsilon Hb\lambda.CHb+\epsilon\omega.c\omega)d} \quad (1)$$

(b) In case of reflection (See FIG. 6b):

$$I\lambda = I_0ar + {}^0(I-r)e^{-\epsilon\omega_1.2dl}\cdot e^{-(\epsilon HbO2\lambda.CHbO2+\epsilon Hb\lambda.CHb+\epsilon\omega C\omega)d} \quad (2)$$

wherein:

$I_0$ represents the intensity of the incident light (made identical irrespective of the wavelength;

$r$ represents the reflectance at the surface of the living tissue (which is regarded as constant irregardless of the wavelength);

$a$ represents the ratio of the light intensity $I_0 \cdot r$ to the measured intensity;

$\epsilon\omega_1$ and $\epsilon\omega_2$ represent light absorption coefficients of the cortical tissues $E_1$ and $E_2$ at the light entering side and the light exiting side, respectively, (which are regarded as independent of wavelength and include the attenuation factor by the scattering), $\epsilon\omega_2 = \epsilon\omega_1$ in case of reflection;

$d_1$ and $d_2$ represents the optical path length of $E_1$ and $E_2$, respectively, $d_2 = d_1$ in case of reflection;

$\epsilon HbO_2\lambda$ and $\epsilon Hb\lambda$ represent the light absorption coefficients of hemoglobin oxide and hemoglobin at wavelength $\lambda$, respectively;

$CHbO_2$ and $CHb$ represent the densities of hemoglobin oxide and hemoglobin, respectively;

$\epsilon\omega$ and $C\omega$ represent the light absorption coefficient of a tissue other than hemoglobin oxide and hemoglobin in the blood layer (which is regarded as independent of the wavelength and includes the attenuation factor by scattering) and its density, respectively; and $d$ represents the optical path length of the blood layer B.

In case of transmission through the tissue, the measured intensity $I\lambda_0$ of light of a standard wavelength $\lambda_0$ is expressed as follows:

$$I\lambda_0 = I_0(1-r)e^{-\epsilon\omega_1.dl}\cdot e^{-\epsilon\omega^{2.d2}\cdot e^{-(\epsilon HbO2\lambda_0.CHbO2+\epsilon Hb\lambda_0 CHB+\epsilon\omega.d\omega)d}}$$

Here, if $I\lambda = I\lambda_0$ at a specific scanning wavelength $\lambda$, $$\frac{I_0(1-r)e^{-\epsilon\omega_1.dl}\cdot e^{-\epsilon\omega2.d2}\cdot e^{-(\epsilon HbO2\lambda.CHbO2+\epsilon Hb\lambda CHb+\epsilon\omega d\omega)d}}{e^{-\epsilon\omega1.dl}\cdot e^{-\epsilon\omega2.d2}\cdot e^{-(\epsilon HbO2\lambda_0.CHbO2+\epsilon Hb\lambda_0CHb+\epsilon\omega d\omega)d}} = I_0(1-r)$$

Namely, $$\epsilon HbO_2\lambda.CHbO_2 + \epsilon Hb\lambda.CHb = \epsilon HbO_2\lambda_0.CHbO_2 + \epsilon Hb\lambda_0 CHb \quad (3)$$

In the case of reflection from the tissue, the measured intensity $I\lambda_0$ is as follows:

$$I\lambda_0 = I_0ar + I_0(1-r)e^{-\epsilon\omega_1.2dl}\cdot e^{-(\epsilon HbO2\lambda_0.CHbO2+\epsilon Hb\lambda_0.CHb+\xi\omega.C\omega)d}$$

So, if $I\lambda = I\lambda_0$, $$I_0ar + I_0(I-r)e^{-\epsilon\omega1.2dl}\cdot e^{-(\epsilon HbO2\lambda_0.CHbO2+\epsilon Hb\lambda_0.CHb+\epsilon\omega C\omega)d} = I_0ar + I_0(1-r)e^{-\epsilon\omega1.2dl}\cdot e^{-(\epsilon HbO2\lambda_0-CHbO2+\epsilon Hb\lambda_0.CHb+\epsilon\omega C)d}$$

Therefore, $$\epsilon HbO_2\lambda.CHbO_2 + \epsilon Hb\lambda.CHb = \epsilon HbO_2\lambda_0.CHbO_2 + \epsilon Hb\lambda_0 CHb$$

This is identical with equation (3) and shows that the equation (3) is good in either case of reflection or transmission.

From equation (3), $$CHbO_2(\epsilon HbO_2\lambda - \xi HbO_2\lambda_0) = CHb(\epsilon Hb\lambda_0 - \epsilon Hb\lambda)$$

And, this equation can be further modified according to the following definitions (4) and (5)

$$\epsilon HbO_2\lambda - \epsilon HbO_2\lambda_0 = kHbO_2\lambda \quad (4)$$

$$\epsilon Hb\lambda - \epsilon Hb\lambda_0 = kHb\lambda \quad (5)$$

Thus, equation (3) can be modified as follows:

$$\frac{CHb}{CHbO_2} = \frac{kHbO_2\lambda}{kHb\lambda}$$

If 1 is added to both terms of this equation, $$1 + \frac{CHb}{CHbO_2} = 1 + \frac{kHbO_2\lambda}{kHb\lambda}$$

which is identical with $$\frac{CHbO_2 + CHb}{CHbO_2} = \frac{kHb\lambda + kHbO_2\lambda}{kHb\lambda}$$

From this equation, $$\frac{CHbO_2}{CHbO_2 + CHb} = \frac{kHb\lambda}{kHb\lambda + kHbO_2\lambda} \quad (6)$$

The lefthand term of equation (6) is identical with the definition of the oxygen saturation. This means that the oxygen saturation can be expressed by values $kHb\lambda$ and $kHbO_2\lambda$ which are defined in formula (4) and (5). In other words, the oxygen saturation can be exclusively expressed by the combination of the known values $\epsilon HbO_2\lambda$, $\epsilon HbO_2\epsilon_0$, $\epsilon Hb\lambda$ and $\epsilon Hb\lambda_0$, wherein $\epsilon$ is determined by the condition $I\lambda = I\lambda_0$ and is free from the influence of troublesome factors such as $I_0$, $r$, $a$, $\epsilon\omega_1$, $\epsilon\omega_2$, $d_1$, $d_2$, $\epsilon\omega$, $C\omega$ and $d$.

In practice, the oxygen saturation is generally measured in accordance with a procedure comprising the steps of:

(a) measuring the intensity of light at a predetermined standard wavelength;

(b) searching for a wavelength at which the light intensity is equal to that of the standard wavelength; and (c) obtaining oxygen saturation from the values $\epsilon HbO_2\lambda$ and $\epsilon Hb\lambda$ at the searched wavelength and the values $\epsilon HbO_2\lambda_0$ and $\epsilon Hb\lambda_0$ at the standard wavelength in accordance with equations (4), (5) and (6).

The above theory will be further explained in connection with FIG. 7, in which curves $\alpha$, $\beta$ and $\gamma$ represent three kinds of different spectral absorption characteristics of hemoglobin with different oxygen saturations, 100 percent, 50 percent and 0 percent, respectively. As is apparent from FIG. 7, the spectral absorption characteristics specifically differ depending on the amount of oxygen saturation of hemoglobin. Additionally, the present invention recognizes the cyclic response of light absorption by various wavelengths and particularly the fact that two or more wavelengths will experience equal absorption for the same level of hemoglobin oxide and hemoglobin. Thus, if 757 nm is selected as the standard wavelength $\lambda_0$, the wavelength $\lambda$ at which the absorption coefficient is equal to that of the standard wavelength 757 nm is 664 nm in case of curve $\alpha$ for oxygen saturation, 100%. Similarly, 700 nm and 708 nm are the wavelengths showing equal absorption coefficient to that of standard wavelength in cases of curves $\beta$ (for oxygen saturation, 50%) and $\gamma$ (for oxygen saturation 0%), respectively. Thus, the wavelength at which the light absorption coefficient is equal to that of the standard wavelength differs in accordance with the oxygen saturation. The wavelength further depends only on the oxygen saturation irrespective of any additional or multiplying noise factors which could be included in the measured light. Thus, in case of FIG. 7, if 644 nm provides the same absorption coefficient, then oxygen saturation is known to be 100%. In other words, the above wavelength and the oxygen saturation correspond to each other on an equal level of signal, irregardless of any white noise factors.

As is apparent from FIG. 7, there is a relatively wide width (66 nm) between the wavelength (644 nm) indicative of the oxygen saturation at 100 percent, and the wavelength (700 nm) indicative of the oxygen saturation at 50 percent, if the standard wavelength is 757 nm. Therefore, various values of oxygen saturation can accurately correspond to their specific wavelengths distributed within a relatively wide width (66 nm) in case of an oxygen saturation range between 50 to 100 percent. On the contrary, there is only a narrow width (8 nm) between the wavelengths, 700 nm and 708 nm, in case of an oxygen saturation range between 50 to 0 percent, and various values of oxygen saturation between 50 to 0 percent would have to be correlated with wavelengths distributed only in the relatively narrow width (8 nm). This means that the measurement of oxygen saturation through the search of wavelength would not be as accurate in the range of oxygen saturation between 50 to 0 percent as it would be in the range of oxygen saturation between 100 to 50 percent when the standard wavelength is selected at 757 nm. Therefore, another different standard wavelength should be selected, in place of 757 nm, if an accurate measurement is desired in the oxygen saturation range between 50 to 0 percent. Further, if a relatively uniform accuracy in the measurement is required in the entire range from 100 to 0 percent of oxygen saturation, then the standard wavelength should be selected balancing the entire range to avoid a biased accuracy.

There may be a case, however, when a desired uniform accuracy within a desired wide range cannot be obtained by only a selection of a single standard wavelength if the requirement is relatively high. Or, there may be another case wherein the search for a wavelength having the same intensity as that of the standard wavelength is relatively difficult in a part of the desired wavelength range if the change in intensity of light corresponding to the change in the wavelength is insufficient.

In the above cases, it is recommended to utilize a second standard wavelength (or third, fourth and additional standard wavelengths, if necessary), in a manner to supplement each other. For example, this can be achieved in the following manner comprising the steps of:

(I) Selecting a first standard wavelength suitable for an accurate measurement in an oxygen saturation range between 100 to 50 percent, and a second standard wavelength suitable for another oxygen saturation range between 50 to 0 percent;

(II) Searching for a first and second wavelength having the same intensity as the first and second standard wavelengths, respectively;

(III) Determining whether or not the first searched wavelength is within a range of wavelengths corresponding to the oxygen saturation range, 100 to 50 percent (or, alternatively, examining whether or not the second searched wavelength is within a range of wavelength corresponding to the oxygen saturation range 50 to 0 percent); and (IV) Deriving an oxygen saturation value corresponding to the first searched wavelength if the answer of the examination is "YES", and deriving an oxygen saturation value corresponding to the second searched wavelength if the answer of the examination is "NO" (or, vice versa in case of the alternative examination).

In the above manner, a uniform high accuracy can be obtained across the whole oxygen saturation range, 100 to 0 percent. Above method can be carried out by the hardware apparatus of the embodiment shown in FIG. 1 to 5 if a software program and the data stored in the ROM of the microcomputer in FIG. 5 is suitably changed.

The following description is directed to a more complex case wherein a third substantial non-white component other than the hemoglobin oxide and the hemoglobin is included in the living tissue. If X represents such a third component, $\epsilon X\lambda$ represents the light absorption coefficient of the third component X at wavelength $\lambda$, and Cx represents the density of the third component X, the following equations, which correspond to equation (3), are obtainable for a pair of standard wavelengths $\lambda_0$ and $\lambda'_0$, respectively, in a similar manner as used in obtaining equation (3) in both the transmission and reflection cases.

$$\epsilon HbO_2\lambda . CHbO_2 + \epsilon Hb\lambda CHb + \epsilon x\lambda Cx = \epsilon H-bO_2\lambda_0 . CHb + \epsilon x\lambda_0 Cx \quad (7)$$

$$\epsilon HbO_2\lambda' . CHbO_2 + \epsilon Hb\lambda' . CHb + \epsilon x\lambda' . Cx = \epsilon H-bO_2\lambda_0' . CHbO_2 + \epsilon Hb\lambda_0' . CHb + \epsilon x\lambda_0' . Cx \quad (8)$$

From equations (7) and (8), the following equations are obtainable, respectively.

$$CHbO_2(\epsilon HbO_2\lambda - \epsilon H-bO_2\lambda_0) + CHb(\epsilon Hb\lambda - \epsilon Hb\lambda_0) + Cx(\epsilon x\lambda - \epsilon x\lambda_0) = 0$$

$$CHbO_2(\epsilon HbO_2\lambda' - \epsilon H-bO_2\lambda_0') + CHb(\epsilon Hb\lambda' - \epsilon Hb\lambda_0') + Cx(\epsilon x\lambda' - \epsilon x\lambda_0') = 0$$

If the following definitions (9) to (14) are introduced:

$$\epsilon HbO_2\lambda - \epsilon HbO_2\lambda_0 = kHbO_2\lambda \quad (9)$$

$$\epsilon Hb\lambda - \epsilon Hb\lambda_0 = kHb\lambda \quad (10)$$

$$\epsilon x\lambda - \epsilon x\lambda_0 = kx\lambda \quad (11)$$

$$\epsilon HbO_2\lambda' - \epsilon HbO_2\lambda_0' = kHbO_2\lambda' \quad (12)$$

$$\epsilon Hb\lambda' - \epsilon Hb\lambda_0' = kHb\lambda' \quad (13)$$

$$\epsilon x\lambda' - \epsilon x\lambda_0' = kx\lambda' \quad (14)$$

the equations are simplified as follows:

$$kHbO_2\lambda . CHbO_2 + kHb\lambda . CHb + kx\lambda . Cx = 0$$

$$kHbO_2\lambda'.CHbO_2 + kHb\lambda'.CHb + kx\lambda'.Cx = 0$$

If, Cx is eliminated by means of this pair of equations, $$(kHbO_2\lambda.kx\lambda' - kHbO_2\lambda'.kx\lambda)CHbO_2 + (kHb\lambda.kx\lambda' - kHb\lambda'.kx\lambda)CHb = 0$$

Therefore, $$\frac{CHbO_2}{CHb} = \frac{kHb\lambda \cdot kx\lambda' - kHb\lambda' \cdot kx\lambda}{kHbO_2\lambda' \cdot kx\lambda - kHbO_2\lambda \cdot kx\lambda'} \quad (15)$$

Similarly, if CHb is eliminated by means of the above pair of simplified equations, $$\frac{CHbO_2}{Cx} = \frac{kx\lambda \cdot kHb\lambda' - kx\lambda' \cdot kHb\lambda}{kHbO_2\lambda' \cdot kHb\lambda - kHbO_2 \cdot kHb\lambda'} \quad (16)$$

In equations (9) to (14), $kHbO_2\lambda$, $kHbO_2\lambda'$, $kHb\lambda$, $kHb\lambda'$, $kx\lambda$ and $kx\lambda'$ are all known. Accordingly, the oxygen saturation can be calculated by equation (15), and the construction ratio between the hemoglobin oxide, hemoglobin and the third component X can be obtainable by equations (15) and (16).

As is apparent from the above description, one oxygen saturation value is exclusively determined when at least one wavelength having an intensity equal to that of at least one standard wavelength is found. Therefore, various oxygen saturation values can be previously calculated in accordance with equations (6) or (15) with respect to various wavelengths and stored in ROM as in the prior embodiment. In this case, oxygen saturation can be obtained by reading out the data stored in ROM by addressing ROM with the searched wavelength.

The present invention is, however, not limited to such an embodiment, but can be embodied by substituting, for the microcomputer having a ROM, a calculation circuit, which actually carries out the calculation of equation (6) or (15) with respect to each wavelength sequentially. Alternatively, the results of the previously calculated oxygen saturation values for various wavelengths can be printed as a sheet or table of values and the person who is informed of the searched wavelength by the device is capable of reading the oxygen saturation from the table by himself. Further, the person who is informed of the searched wavelength by the device can manually calculate the oxygen saturation in accordance with equation (6) or (15) by the aid of a general calculator or computer. In these cases, the device of the present invention is not for providing the actual oxygen saturation, but rather for identifying a specific searched wavelength which can indicate the actual oxygen saturation.

Finally, the optical system of the present invention is not limited to the above-described embodiments, wherein the wavelengths to be measured are sequentially scanned, but could incorporate an optical system wherein all the necessary wavelengths are simultaneously separated into spectra and simultaneously measured in intensity.

It should be noted that the present invention is not only applicable to an oximeter as in the preferred embodiment, but also to other devices for optically analyzing a construction ratio of a known component to another known component, including living tissue of various animals or plants.

As can be readily appreciated, it is possible to deviate from the above embodiments of the present invention, and as will be readily understood by those skilled in the art, the invention is capable of many modifications and improvements within the scope and spirit thereof. Accordingly, it will be understood that the invention is not limited by the specific disclosed embodiments, but only by the scope and spirit of the appended claims.

What is claimed is:

1. An oximeter for obtaining information indicative of the level of hemoglobin oxide in living tissue, comprising:
   a source of light having a plurality of different wavelengths susceptible of coaction with both hemoglobin and hemoglobin oxide;
   means for directing the light at the subject tissue;
   means for measuring the degree of light absorption at a predetermined standard wavelength;
   means for finding a second wavelength in which the degree of absorption is equal to that at the predetermined standard wavelength; and means for determining the level of oxygen saturation in the blood from the second wavelength.

2. The invention of claim 1 wherein said means for determining includes means for storing a plurality of hemoglobin oxide values corresponding to a plurality of respective wavelengths at which the absorption is equal to that of the standard wavelength; means for addressing the stored hemoglobin oxide values in response to the second wavelength, and means for providing an indication of the hemoglobin oxide value of the tissue corresponding to the matched second wavelength.

3. The invention of claim 1 further including filter means for removing any noise components from the signal.

4. The invention of claim 1 wherein said means for finding includes a plurality of band pass filters for selective interaction with the source of light to provide a plurality of wavelengths for finding said second wavelength.

5. The invention of claim 4 further including a rotatable member for supporting the band pass filters and encoding means to generate a position signal indicative of each band pass filter when interacting with the source of light whereby the means for finding can determine a particular second wavelength.

6. An oximeter for measuring an oxygen saturation, which is defined as a ratio of the hemoglobin oxide to the sum of the hemoglobin and the hemoglobin oxide, in living tissue comprising:
   means for providing a source light;
   means for directing the source light at the living tissue;
   means for receiving the source light after coaction with the living tissue;
   means for determining the intensity of the light received by the receiving means at a predetermined standard wavelength;
   means for searching for another wavelength at which the intensity of light received by the receiving means is equal to that of the standard wavelength of light determined by the determining means; and
   means for providing a record of values for the level of hemoglobin oxide as a function of a plurality of wavelengths at which the light absorption of said wavelengths is equal to the absorption at a predetermined standard wavelength;
   and means for finding the level of hemoglobin oxide from the another wavelength in accordance with the preparatorily known recorded valves of hemoglobin oxide.

7. The invention of claim 6 further comprising a second means for determining an intensity of the ligth received by the receiving means at a predetermined second standard wavelength, a second means for searching for a second wavelength at which the intensity of light received by the receiving means is equal to that of the second standard wavelength of light determined by the second determining means, means for examining whether or not the second wavelength is within a predetermined range of wavelengths, and means responsive to the examining means for selecting the second wavelength when it is within the predetermined wavelength range and for selecting said another wavelength when the second wavelength is outside the predetermined wavelength range, and means for using said selected wavelength in said means for determining.

8. An optical analyzer for measuring a construction ratio of the hemoglobin oxide to the sum of the hemoglobin and the hemoglobin oxide to determine oxygen saturation in tissue comprising:
means for providing a source light;
means for directing the source light at the tissue;
means for receiving the source light after contact with the tissue;
means for determining the intensity of the light received by said receiving means at a predetermined standard wavelength;
means for searching for another wavelength at which the intensity of light received by said receiving means is equal to that of said standard wavelength of light determined by said determining means;
means for indicating an oxygen saturation level from said another wavelength including means for storing a plurality of previously known values of oxygen saturation corresponding to respective different wavelengths, and means for taking one oxygen saturation value from said storing means in response to said another wavelength whereby the wavelength found by said searching means is converted into a corresponding level of oxygen saturation for indicating the oxygen saturation in the living tissue.

9. The invention of claim 8, wherein said light source means includes a light exit for directing the source light to the living tissue and said receiving means includes a light entrance for receiving the source light reflected by the living tissue.

10. The invention of claim 8, wherein said light exit and light entrance are positioned so as not to contact the surface of the living tissue.

11. The invention of claim 10, wherein said searching means includes means for sequentially scanning different wavelengths to measure each intensity thereof.

12. A method of optically determining the level of hemoglobin oxide in living tissue by directing predetermined wavelengths of light at the tissue and photoelectrically measuring the light absorption, comprising the steps of:
preparatorily knowing and recording values for a the level of hemoglobin oxide as a function of a plurality of wavelengths at which the light absorption of said wavelengths is equal to the absorption at a predetermined standard wavelength;
measuring the amount of light absorption of the predetermined standard wavelength;
exposing the living tissue to a plurality of differnt wavelengths of light;
determining which of the different wavelength is absorbed to a degree equal to that of the standard wavelength, and
finding the level of hemoglobin oxide from the determined wavelength in accordance with the preparatorily known recorded values of hemoglobin oxide.

* * * * *